United States Patent
Kuboki et al.

(10) Patent No.: US 9,931,380 B2
(45) Date of Patent: Apr. 3, 2018

(54) MEDICAMENT FOR TREATING OLFACTION DISORDER

(71) Applicants: Akihito Kuboki, Tokyo (JP); Shu Kikuta, Tokyo (JP)

(72) Inventors: Akihito Kuboki, Tokyo (JP); Shu Kikuta, Tokyo (JP)

( * ) Notice: Subject to any disclaimer, the term of this patent is extended or adjusted under 35 U.S.C. 154(b) by 0 days.

(21) Appl. No.: 15/046,858

(22) Filed: Feb. 18, 2016

(65) Prior Publication Data

US 2016/0243200 A1    Aug. 25, 2016

(30) Foreign Application Priority Data

Feb. 19, 2015   (JP) .................. 2015-030755

(51) Int. Cl.
- *C07K 14/65* (2006.01)
- *A61K 38/28* (2006.01)
- *A61K 9/00* (2006.01)

(52) U.S. Cl.
CPC ............ *A61K 38/28* (2013.01); *A61K 9/0043* (2013.01)

(58) Field of Classification Search
None
See application file for complete search history.

(56) References Cited

FOREIGN PATENT DOCUMENTS

JP    4263782 B2    2/2009

OTHER PUBLICATIONS

Weinstock, 1993, Physiology & Behavior, 53, 17-21.*
McEntire, 2000, Chem. Senses, 25, 93-101.*
"Abstracts from the XXth Congress of European Chemoreception Research Organization, ECRO-2010, Avignon, France", Chem. Senses, vol. 36, p. E75, 2011.
Komano et al., "Analysis of insulin signaling in the fate decision of granule cells in adult mouse olfactory bulb", Neuroscience Research, vol. 65, Supplement 1, p. S165, 2009.
Kuboki et al., "Nichibi-Shi", vol. 54, No. 3, p. (382)208, Sep. 11, 2015, English language translation.
Lacroix et al., "Insulin But Not Leptin Protects Olfactory Mucosa From Apoptosis", J. of Neuroendocrinology, vol. 23, pp. 627-640, 2011.
McEntire et al., "Olfactory Receptor Neurons in Partially Purified Epithelial Cell Cultures: Comparison of Techniques for Partial Purification and Identification of Insulin as an important Survival Factor", Chem. Senses, vol. 25, pp. 93-101, 2000.

* cited by examiner

*Primary Examiner* — Satyanarayana R Gudibande
(74) *Attorney, Agent, or Firm* — Birch, Stewart, Kolasch & Birch, LLP

(57) ABSTRACT

The object of the present invention is to provide an olfactory disturbance therapeutic agent that is effective in repairing or regenerating olfactory epithelium that suffered damages such as scratches and can be administered for a long time. The object of the present invention is achieved by an olfactory disturbance therapeutic agent including at least one active ingredient that is selected from among a group consisting of insulin, insulin analogs, and insulin secretagogues. Preferably, the olfactory disturbance therapeutic agent is used for people with olfactory disturbance who have, or are at risk of having, impaired insulin secretion or insulin resistance, or for people who could suffer an iatrogenic increase in blood sugar level or a disturbance in a balance of adrenocortical hormone stemming from a long-term use of steroid as olfactory disturbance treatment.

2 Claims, 25 Drawing Sheets

Insulin receptor antibody phospho-Insulin receptor antibody

MEDICAMENT FOR TREATING OLFACTION DISORDER

The present invention relates to an olfactory disturbance therapeutic agent.

CROSS-REFERENCE TO THE RELATED APPLICATIONS

The present application is based upon and claims the benefit of priority from prior Japanese Patent Application No. 2015-30755, filed Feb. 19, 2015, the entire contents of which are incorporated herein by reference.

BACKGROUND OF THE INVENTION

There are various causes for olfactory disturbance, depending on the site of disturbance. In many cases, these are olfactory epithelium-type olfactory disturbance that could happen when such things as swelling or abnormal secretion occur in olfactory epithelium tissues; or mixed-type olfactory disturbance that is attributed to olfactory epithelium and other factors.

The methods to treat such olfactory disturbance include oral therapies that use such drugs as Tsumura Kampo Toukisyakuyaku; and nasal therapies that use steroid drugs such as Nasonex (mometasone furoate hydrate) or Nasal Rinderon A solution (mixture of fradiomycin sulfate and betamethasone phosphate).

However, the use of high-titer steroids, such as Nasal Rinderon A solution, comes with the problems of side effects. For example, among troubles that could happen are moon face, obesity, arteriosclerosis, hyperlipidemia, hypertension, an increase in blood sugar level, effects on the balance of adrenocortical hormone, and virus re-activation for patients infected with Hepatitis B virus. They often become an issue at clinical level. In particular, attention needs to be paid to the use of such drugs for diabetic patients whose number is large. As one that has less side effects, an olfactory disturbance therapeutic agent whose active ingredient is prednisolone derivative is known (Refer to Patent Document 1).

Patent Document 1: Japanese Patent No. 4,263,782

SUMMARY OF THE INVENTION

However, prednisolone derivative belongs to a group of so-called soft steroids. The long-term administration of the substance could lead to side effects similar to those of other steroid drugs.

Accordingly, the object to be achieved by the present invention is to provide an olfactory disturbance therapeutic agent that is effective in repairing or regenerating the olfactory epithelium that suffered damages such as scratches and can be administered for a long time.

As a result of intensive research by inventors to solve the problems, the inventors successfully found, to their surprise, that insulin is remarkably effective in regenerating the olfactory epithelium based on results of in vivo tests using mice, and that insulin can help ameliorate olfactory disturbance.

There had been reports that insulin can boost memory abilities and ameliorate cognitive disorders as it acts not only on sugar metabolism but also on central nerve. However, so far no one has had any idea of insulin having positive effects on the repairing or regeneration of the olfactory epithelium. The findings by the inventors marked the first time the fact has been revealed.

In particular, the homeostasis of olfactory epithelium tissues is regulated by various factors, and is deliberately maintained through life. It is becoming increasingly clear that insulin, as a nerve growth factor, may be playing an important role in maintaining the physiology of nerves. However, how signal transduction via insulin is affecting the behavior of olfactory epithelium cells is not clear at all. However, a link between insulin and the regeneration of olfactory epithelium, which the inventors has found for the first time, is very meaningful from pharmaceutical and medical points of view. The present invention is based on such successful examples and findings.

According to the present invention, what is provided is an olfactory disturbance therapeutic agent that includes at least one active ingredient that is selected from among a group consisting of insulin, insulin analogs, and insulin secretagogues.

Preferably, the olfactory disturbance therapeutic agent is offered in a form of nasal preparation.

Preferably, the olfactory disturbance therapeutic agent is used for people with olfactory disturbance who have, or are at risk of having, impaired insulin secretion or insulin resistance, or for people who could suffer an iatrogenic increase in blood sugar level or a disturbance in a balance of adrenocortical hormone stemming from a long term use of steroid as olfactory disturbance treatment.

The olfactory disturbance therapeutic agent of the present invention increases mature olfactory nerve cells to promote the restoration and regeneration of damaged olfactory epithelium, which leads to a recovery of a lost or reduced sense of smell.

DETAILED DESCRIPTION

Figure 1A:
FIG. 1A is a photo showing DAB-stained olfactory epithelium tissue of a DM mouse 14 days after the administration of methimazole according to an example.

Hereinafter, the present invention will be described in detail.

An olfactory disturbance therapeutic agent of the present invention contains an effective amount of at least one active ingredient that is selected from among a group consisting of insulin, insulin analogs, and insulin secretagogues. The olfactory disturbance therapeutic agent of the present invention can include, as active ingredients, one or two of the insulin, insulin analogs, and insulin secretagogues, or all of them.

The olfactory disturbance therapeutic agent of the present invention can treat or prevent olfactory disturbance of a user by giving the user exogenous insulin or insulin analogues, and/or by administering insulin secretagogues in order to facilitate secretion of endogenous insulin of the user, thereby increasing the concentration of insulin in the user's brain and promoting a differentiation from immature olfactory nerve cells to mature cells and its regeneration and repairing and regenerating olfactory epithelium through an increase in the number of mature olfactory nerve cells. The treatment and prevention includes preventing and delaying the development of ailments or symptoms of the user; reducing the risk of the user developing ailments or symptoms; making a turn for the better as to ailments, symptoms, and conditions; preventing or delaying the worsening of ailments, symptoms, and conditions; and reversing, preventing, and delaying the progression of ailments or symptoms.

Insulin is not limited to a specific substance as long as it is among those known to a person with ordinary skill in the art. For example, one that is known is: CAS No. 9004-10-8. Insulin used in the present invention may be insulin derived from any origin. For example, porcine insulin, bovine insulin, and human insulin are available. Moreover, among those available are pharmaceutically acceptable salts of insulin, such as zinc salt or protamine salt. That insulin may be a mixture of one, two, or more of the above-described substances.

Insulin analogues are not specifically limited, as long as the substances are partially different in structure from insulin; and are coupled with the insulin-like growth factor 1 (IGF-1) receptor, the insulin-like growth factor 2 (IGF-2) receptor, or the glucagon peptide-1 (GLP-1) receptor; and can have an interaction (crosstalk) in a complex insulin cascade initiated by the same insulin activity or insulin signaling as that of insulin. For example, insulin analogues include: insulin in which one to multiple amino acid residues have been replaced with other amino acid residues; insulin that lacks one to multiple amino acid residues; insulin to which one to multiple amino acid residues have been added; hormones that can reinforce or strengthen the insulin signaling action with such gastrointestinal hormones as GLP-1; and nerve growth factors. The meaning of the phrase "one to multiple" includes, for example, one, two, three, four, five, and six; or preferably one, two, three, four, and five; or more preferably one, two, three, and four; or even more preferably one, two, and three. More specifically, insulin analogues may be insulin alpart, insulin lispro, insulin glulisine, insulin degludec, insulin glargine, insulin detemir, and their pharmaceutically acceptable salts. However, insulin analogues are not limited to them. Insulin analogues may be mixtures of one, two, or more of the above-mentioned substances.

The method to acquire insulin and insulin analogues is not specifically limited. For example, the substances can be produced with a gene recombination technology, by isolating and refining from tissues of organisms that secrete insulin or by referencing the amino acid sequence of insulin or by taking other steps. As insulin or insulin analogues, those available in the market may be used. For example, commercially-available insulin preparations, such as those traded under the following brand names (Registered Trademark), may be used without change or in a different administration form: NovoRapid, Novolin, Toreshiba, Levemir, Novopen, Humalog, Humulin, Humapen, Apidora, Lantus, Itango, and Inoretto. Insulin and insulin analogues may be substances that can facilitate secretion of insulin or boost the action of insulin, such as glucagon-like protein (GLP).

Such insulin secretagogues are not specifically limited, as long as the substances facilitate the secretion of endogenous insulin, for example, by inhibiting the ATP-sensitive K+ channel current through stimulation of pancreatic β cell or a binding to sulfonylurea receptors of pancreatic β cells. For example, the substances include nateglinide, mitiglinide, repaglinide, Langerhans-islet activator protein, and glucagon-like peptide. However, the substances are not limited to them. Moreover, insulin secretagogues include substances that can lead to signal transduction mediated by tyrosine kinase that is activated by an insulin-insulin receptor linkage in cells. Insulin secretagogues can be mixtures of one, two, or more of the above-mentioned substances.

The way the insulin secretagogues are acquired is not specifically limited. For example, the substances may be produced by referencing the structural formula or amino acid sequence thereof, or those available in the market may be used.

The content of the active ingredient in the olfactory disturbance therapeutic agent of the present invention is not specifically limited, as long as the amount is enough to increase the number of mature olfactory nerve cells in the olfactory epithelium of a user who has taken the olfactory disturbance therapeutic agent of the present invention. For example, the content may be about 0.001 IU (International Unit) to 1,000 IU a day for a weight of 1 kg, or preferably about 0.01 to about 500 IU, or more preferably 0.1 IU to 10 IU. Moreover, the content of the active ingredient in the olfactory disturbance therapeutic agent of the present invention can be about 0.01 IU to 500 IU a day, or preferably 0.1 IU to 200 IU, for example. 1 IU represents 1 International Unit of human insulin (gene recombination). If the active ingredient is insulin analogue, its amount is equal to the above-mentioned IUs. If the active ingredient is insulin secretagogues, the amount is set at a level that can secrete the quantities of insulin in a living body that are equal to the above-mentioned IUs.

If the olfactory disturbance therapeutic agent of the present invention contains insulin or insulin analogues, the agent is administered parenterally. If the olfactory disturbance therapeutic agent contains insulin secretagogues, the agent is administered orally or parenterally depending on the characteristics of the substance.

The olfactory disturbance therapeutic agent of the present invention is not specifically limited in terms of an administration route thereof. The amount of the agent to be administered can be kept small if the administration is conducted near an affected area. This can prevent the side effects, such as low blood sugar. Therefore, it is preferred that the agent be nasally administered. Accordingly, the olfactory disturbance therapeutic agent of the present invention is preferably in the form of nasal drops or eye drops, or more preferably in the form of nasal drops.

The olfactory disturbance therapeutic agent of the present invention may consist only of active ingredients, or may contain any ingredients other than the active ingredients. For example, if the olfactory disturbance therapeutic agent of the present invention is offered in the form of nasal drops, the other ingredients include additives that are known to a person having ordinary skill in the art and commonly used in the nasal drops. More specifically, the other ingredients include preservatives, isotonizing agents, buffering agents, stabilizing agents, pH adjusting agents, thickeners, and suspending agents.

For example, the preservatives include parabens (methyl parahydroxybenzoate, propyl parahydroxybenzoate, and the like); invert soaps (benzalkonium chloride, benzethonium chloride, chlorhexidine gluconate, cetylpyridinium chloride, and the like); alcohol derivatives (phenethyl alcohol, and the like); organic acids and salts thereof (sodium dehydroacetate, sorbic acid, salts thereof, and the like); phenols (parachloromethoxyphenol, parachlorometacresol, and the like); and organic mercury agents (thimerosal, phenylmercuric nitrate, nitromezol, and the like). For example, the isotonizing agents include sodium chloride, sorbitol, concentrated glycerin, and mannitol.

For example, the buffering agents include boric acid and salts thereof, phosphates, acetates, and amino acid salts.

For example, the stabilizing agents include antioxidants (sodium sulfite, sodium bisulfite, sodium metabisulfite, and the like); and chelating agents (sodium edetate, and citric acid and salts thereof).

For example, the pH adjusting agents include hydrochloric acid, acetic acid, sodium hydroxide, and phosphoric acid.

For example, the thickeners include sugars (sorbitol, mannitol, sucrose, and the like); celluloses (methyl cellulose, carboxymethyl cellulose sodium, hydroxypropyl methylcellulose, and the like); and synthetic polymers (polyvinyl alcohol, polyvinylpyrrolidone, carboxyvinyl polymer, and the like).

For example, the suspending agents include the above-mentioned celluloses; synthetic polymer compounds; crystalline cellulose/carmellose sodium; and surfactants (cationic surfactants such as quaternary ammonium salts, anionic surfactants such as alkyl sulfate, Polysorbate 80, polyoxyethylene hardened castor oil, non-ionic surfactants such as tyloxapol, amphoteric surfactants such as lecithin, and the like).

The amount of the additives to be used is to be set appropriately by a person of ordinary skill in the art, and is not specifically limited. If the olfactory disturbance therapeutic agent of the present invention is offered in the form of nasal drops, it is preferred that the agent be in a state similar to the physiological state of the nose (or in the state of being isotonic to nasal discharge). For example, the osmotic pressure is in the range equivalent to 0.2 to 4.0 w/v % of saline solution; or preferably in the range equivalent to 0.5 to 2.0 w/v % of saline solution; or more preferably in the range equivalent to 0.8 to 1.5 w/v % of saline solution.

If the olfactory disturbance therapeutic agent of the present invention is used in the form of nasal drops, for example, its pH is in the pH range that is usually used for typical nasal drops. Specifically, its pH is 5 to 7; its osmotic pressure is within the range of osmotic pressure that is usually used for typical nasal drops, and, more specifically, the osmotic pressure is 140 to 1,140 mOsm, or more preferably 200 to 870 mOsm, or more preferably 280 to 310 mOsm; its viscosity is in the range of viscosity that is usually used for typical nasal drops, and, more specifically, the viscosity is less than or equal to 25,000 cps, or preferably 5,000 to 1 cps.

The olfactory disturbance therapeutic agent of the present invention can contain, as the other ingredients, other olfactory disturbance therapeutic agents, other medicinal preparations, or their active ingredients. For example, among such substances are non-steroidal anti-inflammatory agents, antihistamines, anti-allergic agents, antibiotics, vasoconstrictors, antihypertensive agents, and their active ingredients.

The olfactory disturbance therapeutic agent of the present invention may contain sugars and sugar analogs depending on the amount being administered or the way the agent is given, in order to prevent a user from being exposed to the risk of low blood sugar due to the effect of active ingredients; or the olfactory disturbance therapeutic agent of the present invention may be used together with sugars and sugar analogs.

After being administered to a user, the olfactory disturbance therapeutic agent of the present invention promotes the differentiation, growth and/or regeneration of immature olfactory nerve cells. As a result, the olfactory disturbance therapeutic agent induces an increase in the number of mature olfactory nerve cells in olfactory epithelium and the repair or regeneration of olfactory epithelium. In this manner, olfactory disturbance can be treated. Moreover, the active ingredients of the olfactory disturbance therapeutic agent of the present invention are not steroidal compounds. Therefore, the olfactory disturbance therapeutic agent of the present invention is free of side-effect problems associated with the administration of steroid drugs, and is suitable for a long-term administration.

The way the olfactory disturbance therapeutic agent of the present invention is used is not specifically limited. The olfactory disturbance therapeutic agent can be appropriately used depending on the form thereof. For example, if the olfactory disturbance therapeutic agent of the present invention is offered in the form of nasal drops, the olfactory disturbance therapeutic agent can be used by following the method usually used for commonly-known nasal drops. In this case, for example, the olfactory disturbance therapeutic agent can be used by falling-drop method, among other things. More specifically, two to three drops of the olfactory disturbance therapeutic agent of the present invention are dropped into both nasal cavities when a user is being in a suspended head position. The position is kept for 5 to 10 minutes. This operation is conducted twice a day in the morning and evening.

The dosing interval of the olfactory disturbance therapeutic agent of the present invention can be appropriately selected depending on the amount being given or the administration form thereof; the dosing interval is not specifically limited. For example, 0.1 to 10 U/kg (0.1 to 10 IU/kg) of the active ingredients are administered nasally twice a day for a period of 7 days or more, or preferably for a period of 10 days or more, or more preferably for a period of 14 days or more.

Users of the olfactory disturbance therapeutic agent of the present invention are not specifically limited. For example, the users may include human beings such as infants, toddlers, children, adolescents, and adults. For example, the olfactory disturbance therapeutic agent of the present invention may be used in mammals such as cats, dogs, cows, and horses.

Usually, healthy people can secrete insulin in their bodies. However, like patients with diabetes, there are some who have trouble secreting insulin or those who have resistance against insulin. Accordingly, the olfactory disturbance therapeutic agent of the present invention is preferably used for people with olfactory disturbance who have trouble secreting insulin or who have resistance against insulin; or who are at the risk of being exposed to such troubles; or who could suffer an iatrogenic increase in blood sugar level or a disturbance in a balance of adrenocortical hormone stemming from a long term use of steroid as olfactory disturbance treatment. The olfactory disturbance therapeutic agent of the present invention is more preferably used for middle-aged or elderly people; or people with a lack of exercise who are at the risk of metabolic syndrome, including type 2 diabetes.

Hereinafter, examples of the present invention will be described in more detail. However, the present invention is not limited to those examples. As long as the problems of the present invention can be resolved, the present invention may be embodied in various forms.

EXAMPLES

As described below, the in vivo tests that use mice have demonstrated that insulin is remarkably effective in ameliorating olfactory disturbance.

[I. Effect of Ameliorating Olfactory Disturbance by Insulin Administration for Model Mice with Type 1 Diabetes (1)]

1. Creation of Model Mice (DM or STZ Mice) with Type 1 Diabetes

To C57BL/6 mice (normal mice; Japan SLC, Inc) at the age of 10 weeks, 120 mg/kg of streptozotocin (STZ; Sigma-Aldrich) was administered intraperitoneally for three days in a row, on Days 0 (Initial administration), 1, and 2. On Day 7, those with a fasting blood glucose (fasting blood sugar level: FBS) of 250 mg/dl or more were defined as DM mice in which pancreatic β cells were specifically impaired. Moreover, subsequent operations used those with a blood sugar of more than 250 mg/dl at any time after about one week since the administration of STZ.

2. Creation of Model Mice with Olfactory Disturbance

To each of positive control mice, which were created by giving only physiological saline to normal mice, and DM mice, 80 mg/kg of methimazole (Siyma-Aldrich) was administered intraperitoneally in order to create model mice with olfactory disturbance. The model mice with olfactory disturbance were created as metabolites of methimazole selectively damaged olfactory epithelium. The mechanism of olfactory disturbance is considered to be the activation of caspase that induces apoptosis in olfactory cells. When normal mice were given methimazole, the damaged olfactory epithelium could recover to the almost normal level about 28 days after the administration. Moreover, normal mice that were given physiological saline instead of methimazole were used as control. Their weight and blood sugar levels of tail veins were measured 28 days after the methimazole injection.

3. Immunohistochemistry

The hearts of mice were perfused with 4% paraformaldehyde in 0.1M phosphate buffer. The mice were sacrificed and fixed 24 hours later with the same fixative. Nostril tissues containing OE were decalcified with a 10% EDTA solution (pH 7.0), and were embedded in paraffin. Coronal sections (with thickness of 4 μm) were cut off and put on silane-coated slides. The deparaffinized sections were autoclaved for 10 minutes in Target Retrieval Solution (S1700; Dako) for antigen retrieval. Immunohistochemistry was conducted with one of the following antibodies: Anti-insulin receptors, anti-phosphorylated insulin receptors, anti-olfactory marker proteins (OMP, goat polyclonal, 1:4000 dilution; Wako Chemicals), anti-activated caspase-3 (rabbit polyclonal, 1:5000; Cell Signaling Technology), anti-Ki-67 (mouse monoclonal, 1:500; BD Biosciences), and anti-c-fos antibodies (Rabbit IgG, 1:1000; Santa Cruz Biotechnology).

With the use of Histofine Simple Stain MAX-PO Second Antibody System (Nichirei), as for anti-OMP (goat), anti-activated caspase-3 (rat), anti-Ki-67 (mouse) and anti-c-fos (rabbit), immune reactions were detected. With the use of anti-OMP (anti-OMP antibody, goat polyclonal, 1:4000; Wako Chemicals) and anti-caspase-3 (anti-activated caspase-3 antibody, rabbit polyclonal, 1:5000; Cell Signaling Technology) antibodies, primary antibodies were used for double immunostaining.

After being washed, the tissues were incubated for one hour at room temperatures together with donkey anti-goat Alexa Fluor 488 and donkey anti-rabbit Alexa Fluor 594 (1:100; Invitrogen).

4. Analysis

In order to suppress the variation of data values that could be caused by anatomical changes (e.g. aerated nasal turbinate) between mice and in the mice, the OE analysis was conducted in such a way as to be limited to OE (olfactory epithelium) of the nasal septum and nasal turbinate's top on the right and left sides in the nasal cavity.

Sections were cut at intervals of 500 μm. The olfactory epithelium included the following two cell lines: Olfactory nerve cells (OSNs) and basal stem cells. Rectangular cells on lamina propria in OE were defined as basal cells. The rest of the cells were defined as OSNs. The thickness, or distance from the lamina propria to the surface, was measured with software known as ImageJ. The number of OSNs labeled with anti-OMP, anti-activated caspase-3, and anti-Ki-67 antibody was quantitatively analyzed by uniquely immunostaining for each antigen and using sections counterstained with hematoxylin. As for connective tissues under the lamina propria, the immunostaining of cells with an intermediate background intensity more than double the standard deviation was regarded as being positive. The number of OSNs and the number of immunostained cells (OMP-positive cells, Ki-67-positive cells, and caspase-3 positive cells) were measured along the total length of the nasal septum in microscopic observation images (of each of normal groups and STZ groups) for both the left and right sides. The average of the measured values and the standard deviation were calculated in each of the groups for each 100 μm-length portion of the nasal septum as for the number of OSN, OMP-positive cells and Ki-67-positive cells; and the number of caspase-3 positive cells was determined per length of the nasal septum.

It was nearly impossible to count the number of olfactory cells on the entire olfactory epithelium inside the nose. Given the fact that all olfactory nerves extending from the entire region of the olfactory epithelium converges on the olfactory bulb, it can be said, as a result of observing the entire region of the olfactory bulb, that the phenomenon does not occur only in part of the olfactory epithelium, but that a similar phenomenon occurs across the entire olfactory epithelium. Accordingly, the tissues of the entire olfactory bulb were observed.

Figure 6A:
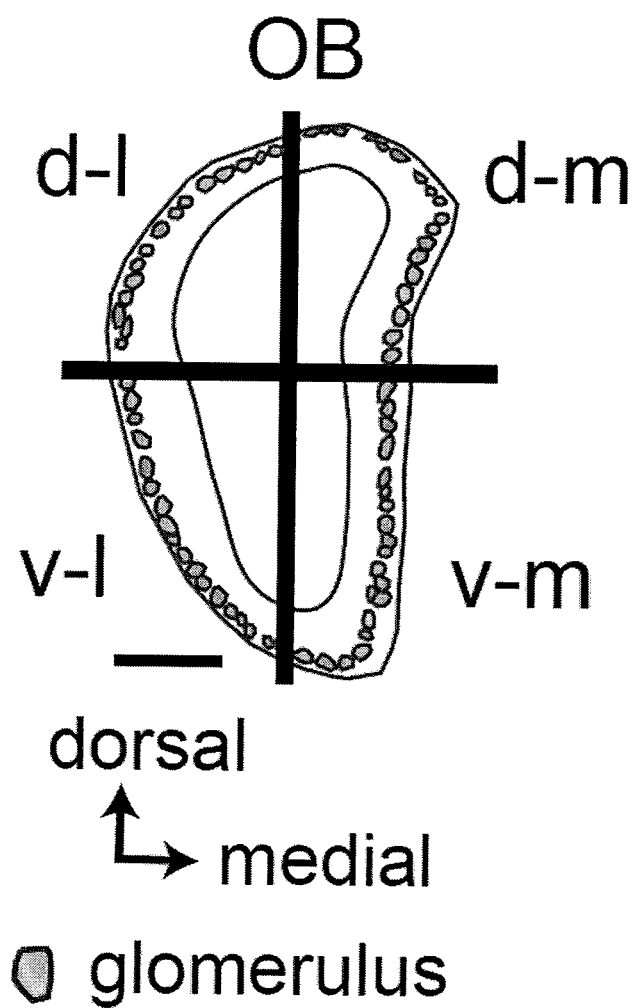
FIG. 6A is a diagram schematically showing coronal sections of OB according to an example.

For each OB, one coronal section was selected from the central region of the OB. Then, seven glomerular pieces were selected at random in individual sections of OB (Refer to FIG. 6A). Significant OMP-stained regions were defined as those whose staining was more than double the standard deviation of the average of background intensities inside the external plexiform layer of OB.

The percentage of significant OMP-stained regions, or the area of significant OMP-stained regions, was divided by the total area of glomerulus (OMP-stained area/Glomerular area×100). In this manner, the calculation was conducted on glomerulus. An analysis of immunostained regions was carried out with software known as ImageJ.

5. Statistical Analysis

Statistical analysis was carried out with Mann-Whitney U test (STZ mice vs normal mice; after being disabled and given physiological saline). Error bars represent the mean±SD. The p-value that was less than 0.05 was regarded as statistically significant.

6. Assessment of how Much Normal Mice and DM Mice Recover from Olfactory Disturbance Mice (n=7) that were given methimazole 3 days, 7 days, 14 days, and 28 days ago were sacrificed with urethane anesthesia, and olfactory epithelium tissues were taken out. The olfactory epithelium tissues were turned into coronal sections, from the head of the mouse to the front of olfactory bulb. The created sections were stained with hematoxylin-eosin (HE). In this manner, in the nasal septum and the top portion of the nasal turbinate, the thickness of olfactory epithelium and the number of olfactory nerve cells (OSNs) were measured and assessed. As for the number of olfactory nerve cells, during the assessment of the number of mature olfactory nerve cells, anti-OMP (olfactory marker protein; Wako Chemicals) antibodies were used. During the assessment of division capacities of basal cells, anti-Ki-67 antibodies (BD Biosciences) were used for immunostaining. Incidentally, as for the division capacities of basal cells, because the basal cells serve as a source and growth and differentiation into mature olfactory nerve cells would occur, the spare and potential capacities for the repair of olfactory epithelium were assessed.

Figure 1B:
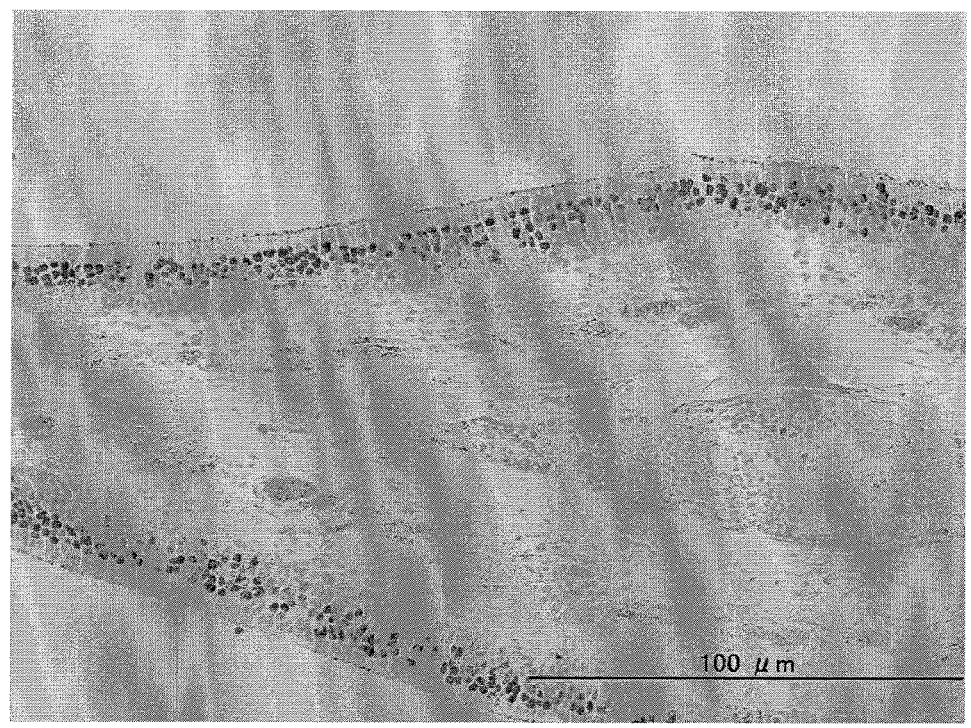
FIG. 1B is a photo showing DAB-stained olfactory epithelium tissue of a normal mouse 14 days after the administration of methimazole according to an example.

The results show that, up until the $7^{th}$ day after the administration of methimazole, there was no significant difference between normal and DM mice in each of the items, the thickness of olfactory epithelium and the numbers of OSNs and mature olfactory nerve cells. However, on the $14^{th}$ day after the administration of methimazole, DM mice clearly showed a decrease in the thickness of olfactory epithelium and the numbers of OSNs and mature olfactory nerve cells (the number of OMP-positive cells), compared with normal mice (Refer to FIGS. 1A, 1B, and 3A to 3C). That is, in the case of FIG. 1A, there was almost no OMP-positive cells (brown-stained portions), indicating that there were almost no mature olfactory nerve cells. Meanwhile, FIG. 1B shows a large number of OMP-positive cells.

Figure 2A:
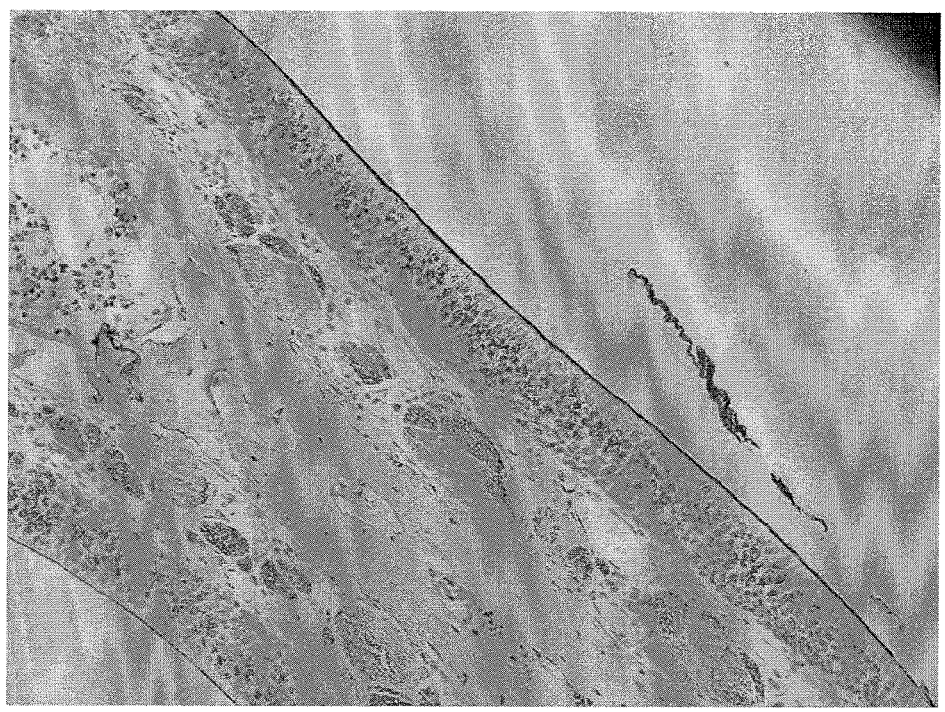
FIG. 2A is a photo showing DAB-stained olfactory epithelium tissue of a DM mouse 28 days after the administration of methimazole according to an example.
Figure 2B:
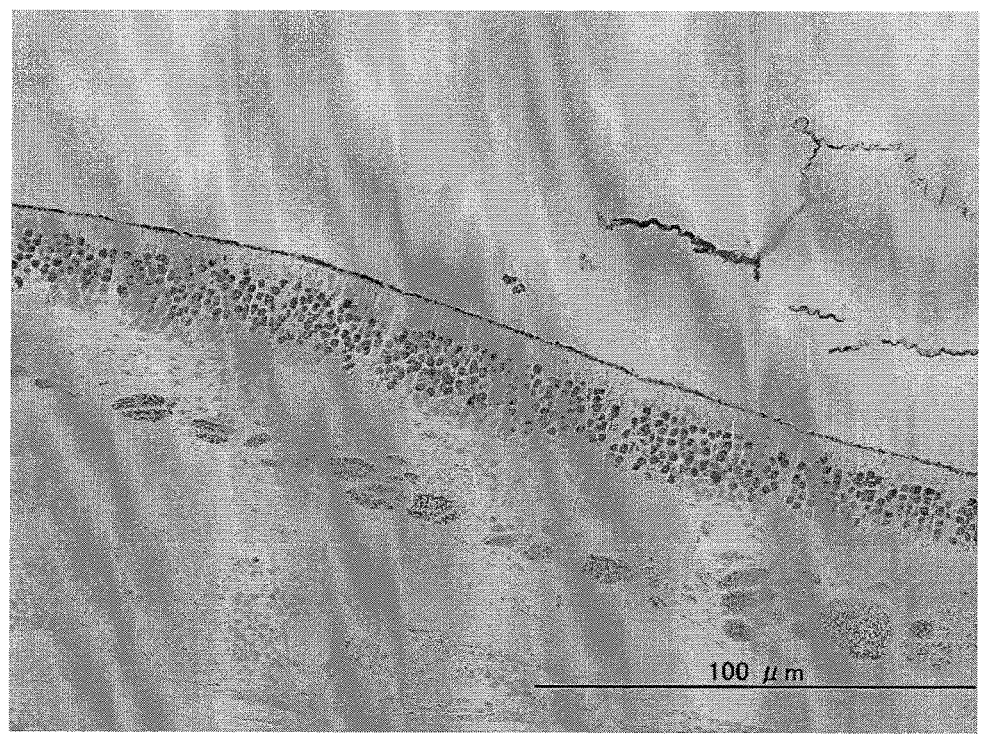
FIG. 2B is a photo showing DAB-stained olfactory epithelium tissue of a normal mouse 28 days after the administration of methimazole according to an example.

On the $28^{th}$ day after the administration of methimazole, similar results were obtained (Refer to FIGS. 2A, 2B, and 3A to 3C). That is, while FIG. 2A shows small numbers of almost all OMP-positive cells, FIG. 2B shows that almost all olfactory nerve cells were OMP-positive.

Figure 3A:
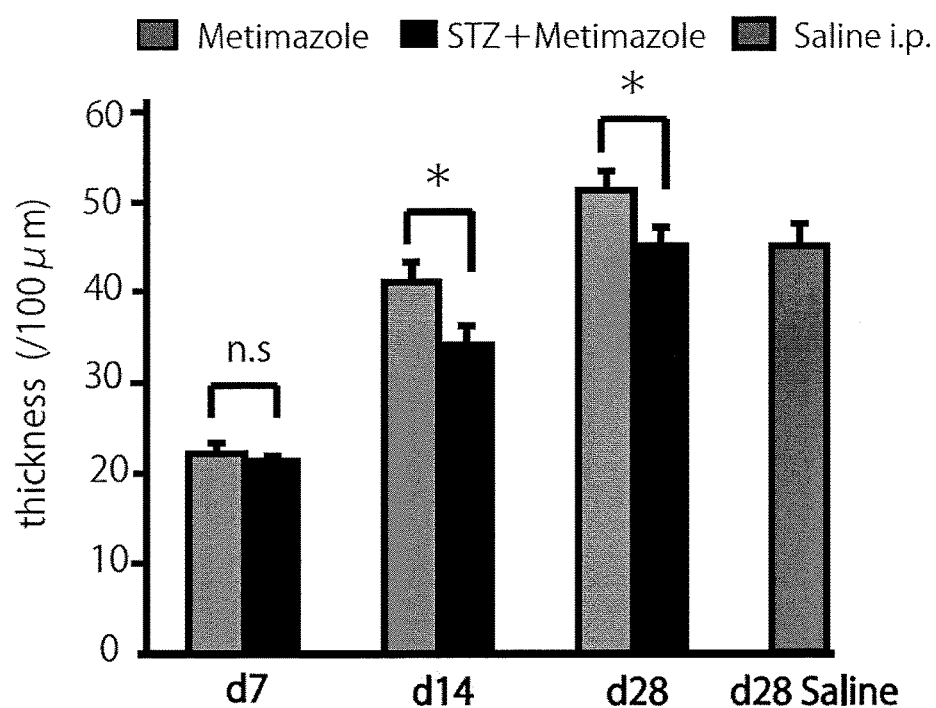
FIG. 3A is a diagram showing the results of evaluation on the thickness of olfactory epithelium 7 days, 14 days, and 28 days after the administration of methimazole according to an example (In the diagram, "Met" means a normal mouse fed with methimazole; "STZ+Met" indicates a DM mouse fed with methimazole; and "d28 Saline" shows the results of a normal mouse being fed with a normal saline solution instead of methimazole. Moreover, the figures are average values (n=7), and the bar represents standard deviation. "*" indicates that it has been judged by a Mann-Whitney's U test that there is a significant difference between the values of normal and DM mice because of a risk rate of 5%. "n.s" means that it has been judged that there is no significant difference)
Figure 3B:
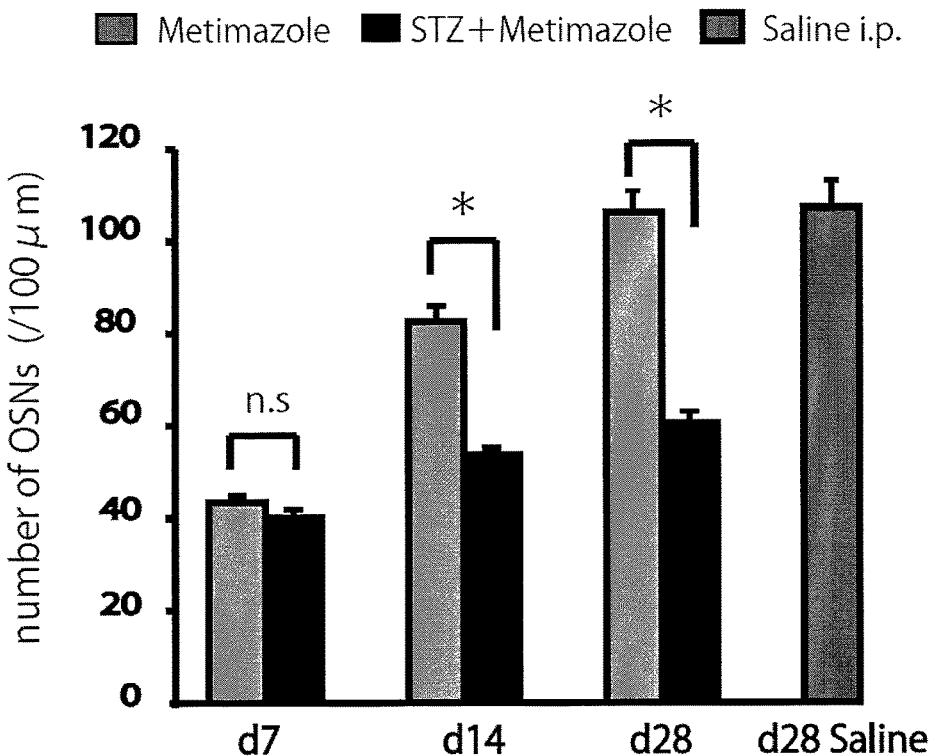
FIG. 3B is a diagram showing the results of evaluation on the number of olfactory nerve cells 7 days, 14 days, and 28 days after the administration of methimazole according to an example (The meanings of symbols in the diagram are similar to those in FIG. 3A)
Figure 3C:
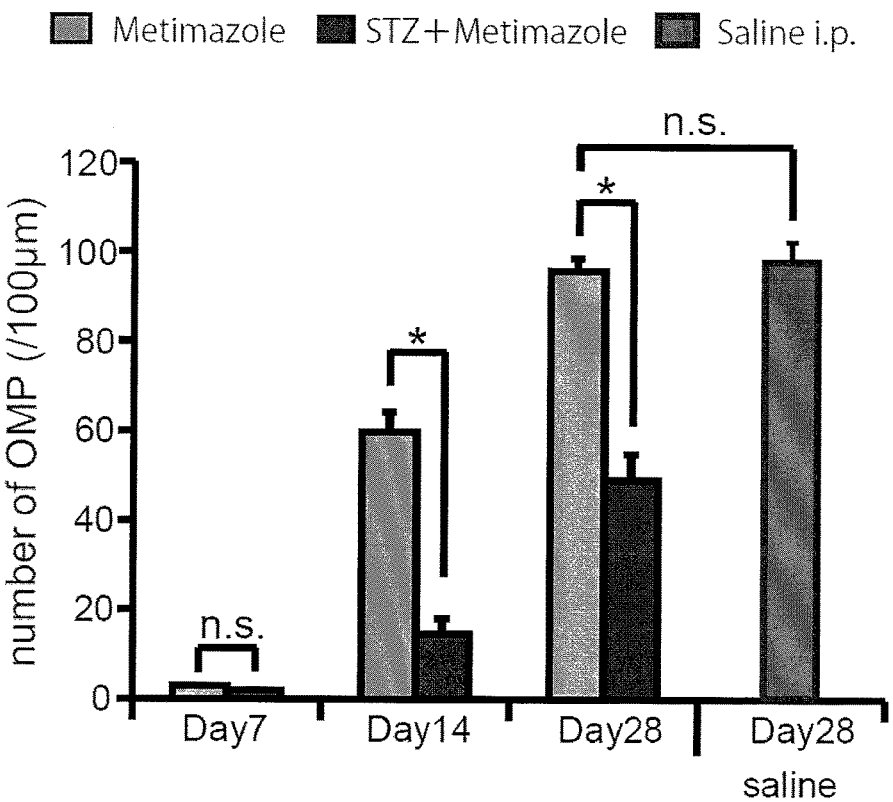
FIG. 3C is a diagram showing the results of evaluation on the number of OMP-positive cells 7 days, 14 days, and 28 days after the administration of methimazole according to an example (The meanings of symbols in the diagram are similar to those in FIG. 3A)

After the 14$^{th}$ day since the administration of methimazole, it was found that DM mice suffered significant decreases in the thickness of olfactory epithelium and the numbers of OSNs and mature olfactory cells (the number of OMP-positive cells) (FIGS. 3A to 3C). The results mean that, after the 14$^{th}$ day of disturbance corresponding to the synapse formation stage, it was found that DM mice suffered significant drops in the thickness of olfactory epithelium and the number of olfactory cells.

7. Assessment of DM Mice with Long-Term Insulin Secretion Insufficiency

Figure 4A:
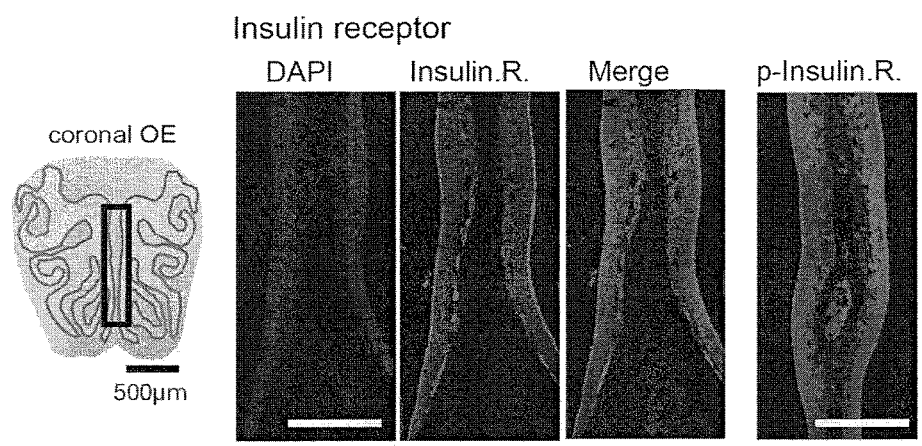
FIG. 4A shows the results of histological staining with the use of DAPI, Insulin R, and Merge on olfactory epithelium tissue of a normal mouse according to an example.

Olfactory epithelium tissues were taken from normal mice, and fixed sections were created. After that, the sections were histologically stained with DAPI, Insulin R, and Merge (Refer to FIG. 4A). It was confirmed from FIG. 4A that insulin receptors and phosphorylated insulin receptors were expressed across the entire olfactory epithelium of normal mice (p-Insulin R). There had been no reports of insulin receptors being expressed across the entire olfactory epithelium. The latest findings suggest that insulin signaling may be playing some important role in maintaining the homeostasis of the olfactory epithelium.

Figure 4B:
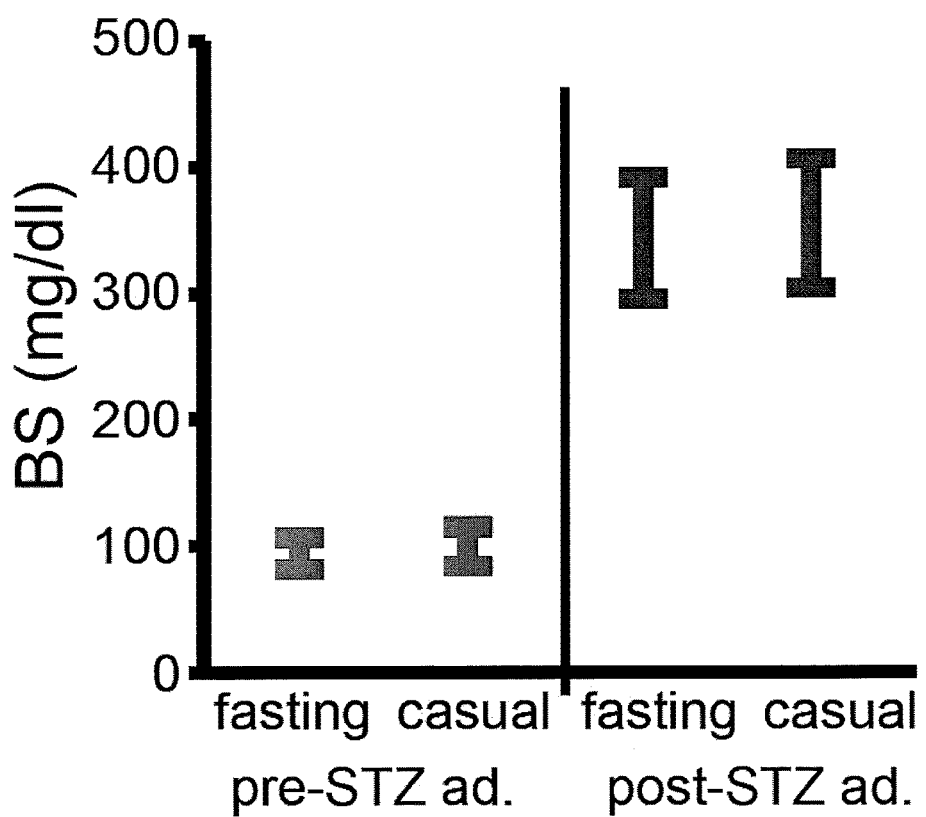
FIG. 4B shows the results of a study on the level of blood sugar in a DM mouse according to an example.
Figure 4C:
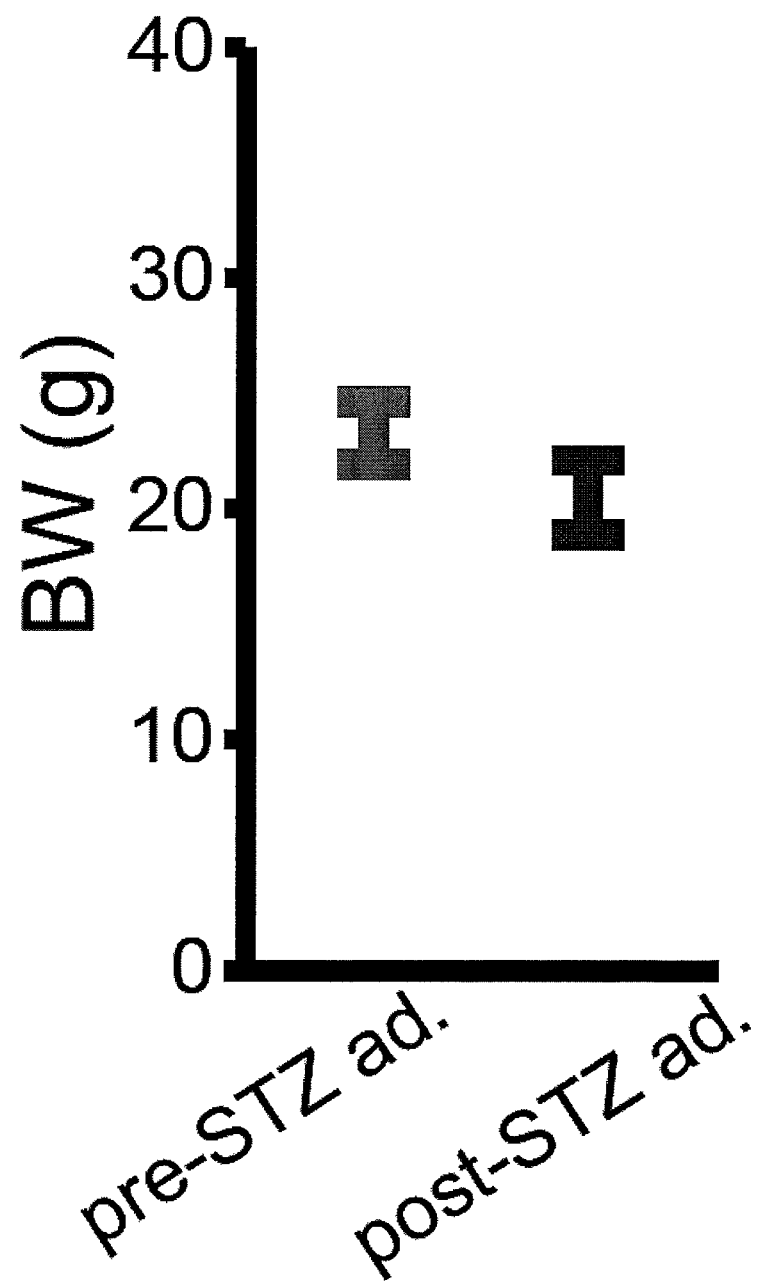
FIG. 4C shows the results of a study on the weight of a DM mouse according to an example.

The blood sugar level and weight of DM mice were examined (Refer to FIGS. 4B and 4C). It was found that DM mice (post-STZ ad.) showed a significant increase in the blood sugar level during fastening (fastening) or normal (casual) time, compared with normal mice (pre-STZ ad.) (Refer to FIG. 4B). Moreover, it was also confirmed that, compared with normal mice, DM mice slightly lost weight, apparently due to polyuria associated with diabetes (Refer to FIG. 4C).

Figure 4D:
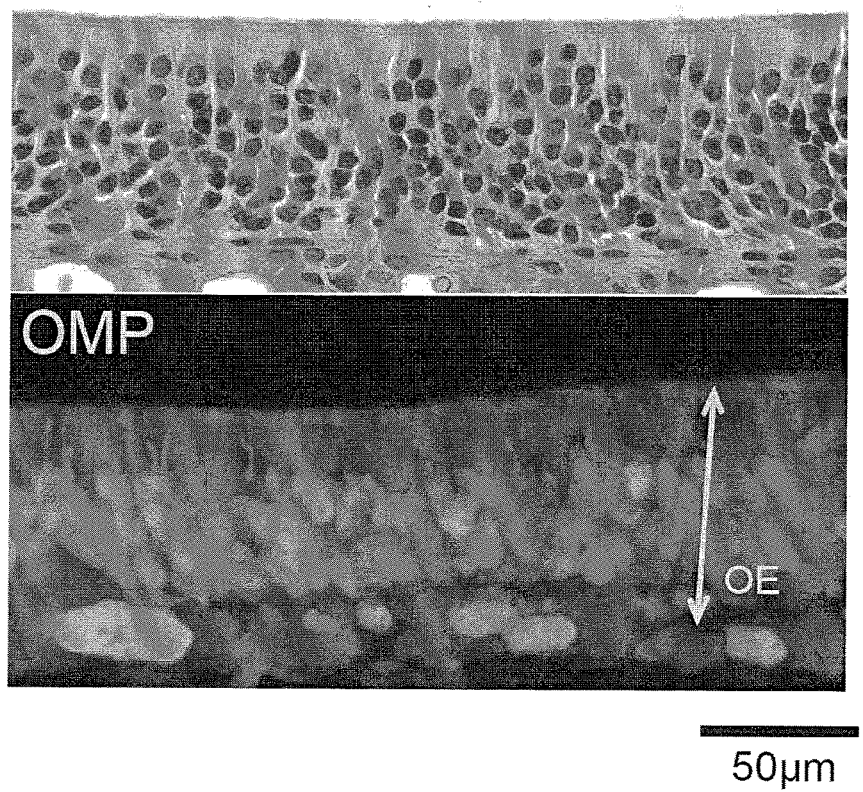
FIG. 4D shows the results of HE straining, as well as of identifying the number of OMP-positive cells, for coronal sections of olfactory epithelium tissue of a DM mouse 28 days later, according to an example.
Figure 4E:
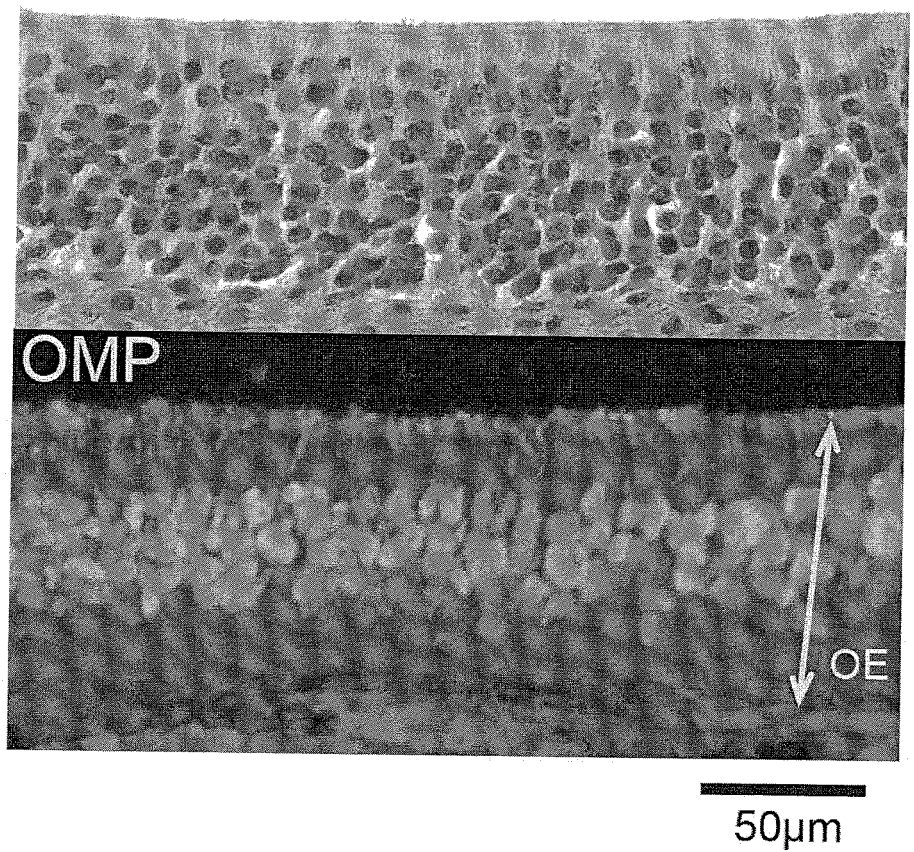
FIG. 4E shows the results of HE straining, as well as of identifying the number of OMP-positive cells, for coronal sections of olfactory epithelium tissue of a DM mouse 90 days later, according to an example.

In order to confirm whether a long-term insulin secretion insufficiency itself could make an impact on the olfactory epithelium, DM mice were given physiological saline instead of methimazole (Day 0), and a follow-up observation was conducted on Day 28 and Day 90. FIGS. 4D and 4E show the results of HE staining on coronal sections of the olfactory epithelium tissues on Day 28 and Day 90, as well as the results of confirming the number of OMP-positive cells. As shown in FIGS. 4D and 4E, as for the olfactory epithelium of STZ mice, there were no changes in the thickness of the olfactory epithelium and the number of olfactory cells even after about one month or three months. The results prove that the decline in insulin over about 3 months did not induce any histological changes in the olfactory epithelium.

Figure 5A:
FIG. 5A shows the results of immunostaining with insulin receptor antibody and phosphorylated insulin receptor antibody for a model mouse with olfactory disturbance after the administration of methimazole according to an example.
Figure 5A:
Figure 5B:
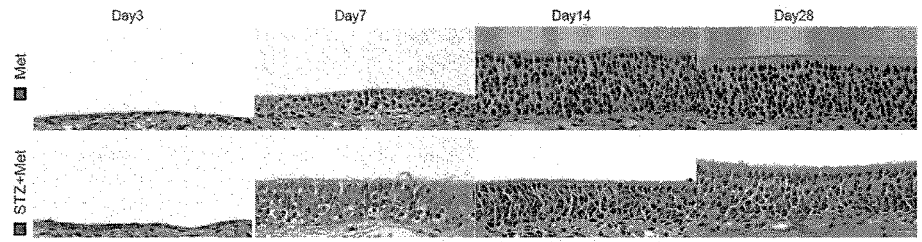
FIG. 5B shows the result of HE straining on olfactory epithelium for a model mouse with olfactory disturbance after the administration of methimazole according to an example.

FIG. 5A shows the results of immunostaining model mice with olfactory disturbance with an insulin receptor antibody and a phosphorylated insulin receptor antibody 3 days, 7 days, and 14 days after the administration of methimazole. The results confirmed that, in the entire period during which a full maturity has been achieved since the onset of olfactory epithelium disturbance, the insulin receptor and the phosphorylated insulin receptor were being expressed across the entire olfactory epithelium at the level of basal stem cells. FIG. 5B shows the results of HE staining on model mice with olfactory disturbance 3 days, 7 days, 14 days, and 28 days after the administration of methimazole. As shown in FIG. 5b, in the Met group in which normal mice were given methimazole, the olfactory epithelium tissues recovered to the normal level of the olfactory epithelium 28 days after the onset of the disturbance. Incidentally, in STZ+Met, the olfactory epithelium was still slightly thin even 28 days after the onset of the disturbance, with a smaller number of OSNs. The results of FIG. 5B are shown in FIGS. 3A and 3B. The results of FIG. 5C are shown in FIG. 3C.

Figure 5C:
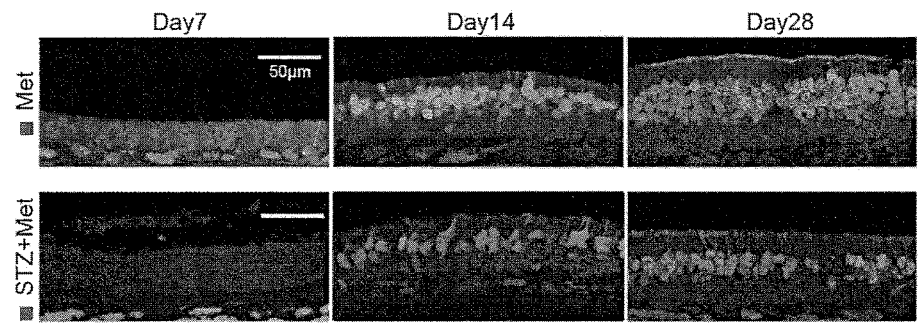
FIG. 5C shows the results of immunostaining with OMP antibody on olfactory epithelium for a model mouse with olfactory disturbance after the administration of methimazole according to an example.
Figure 5D:
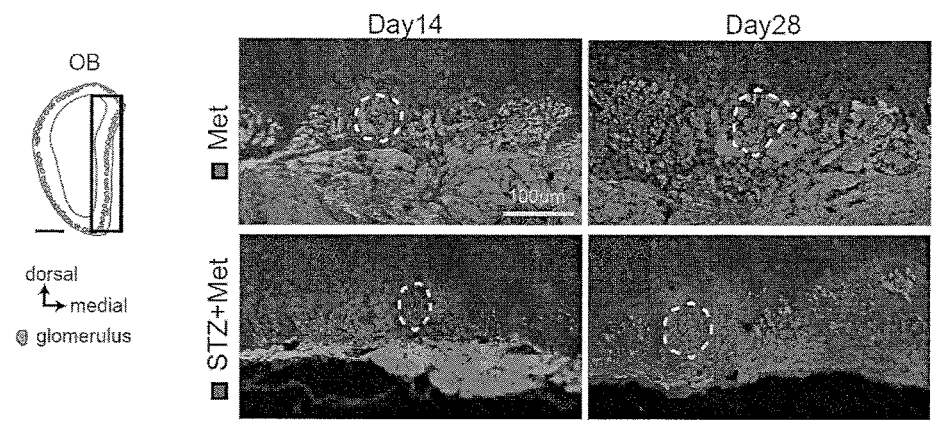
FIG. 5D shows the results of analysis of OMP positive areas of olfactory bulb (OB) for a model mouse with olfactory disturbance after the administration of methimazole according to an example.
Figure 5E:
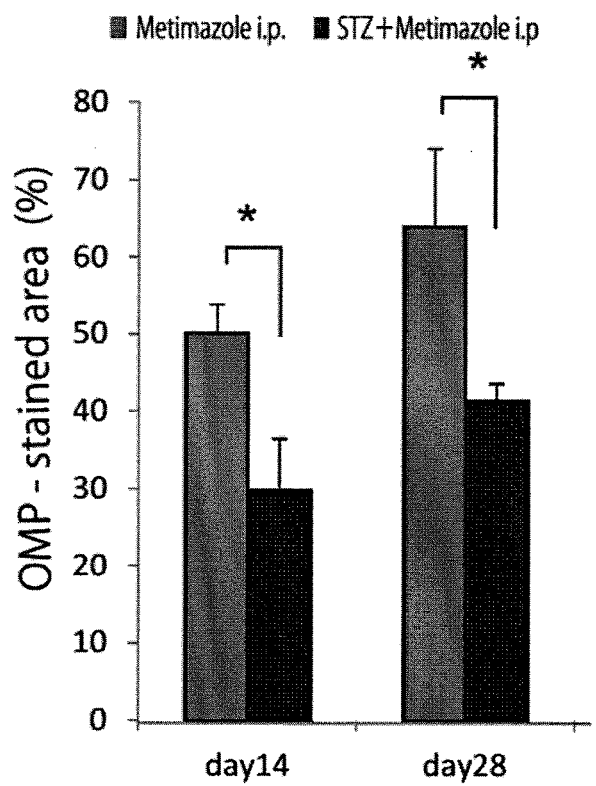
FIG. 5E shows the results of analysis of OMP positive areas of olfactory bulb (OB) for a model mouse with olfactory disturbance after the administration of methimazole according to an example.

FIG. 5C shows the results of immunostaining model mice with olfactory disturbance with an OMP antibody 7 days, 14 days, and 28 days after the administration of methimazole. As shown in FIG. 5C, in the group of STZ mice, there was a significant drop in the number of OMP-positive cells, which are a mature olfactory cell marker, about two weeks after the onset of olfactory epithelium disturbance (which corresponds to a period in which olfactory nerves form olfactory bulbs and synapses). After that, the delay in the regeneration continued in the STZ mice. FIGS. 5D and 5E show the results of analysis on OMP-positive regions of model mice with olfactory disturbance 14 days and 28 days after the administration of methimazole. As shown in FIGS. 5D and 5E, the results similar to those shown in FIGS. 5C and 3C were detected in the OMP-positive regions of the olfactory bulbs.

8. Summary

The long-term reduction of insulin did not cause histological changes to the olfactory epithelium where mature olfactory cells were dominant. However, when the olfactory epithelium was in the regeneration process with nascent, immature olfactory cells after suffering the disturbance, it was observed that the regeneration of the olfactory epithelium was remarkably delayed. The results suggested that insulin signaling could play a very important role in the post-disturbance homeostatic regeneration process instead of maintaining the homeostasis of physiological olfactory epithelium. Particularly, the results raise the possibility of increased dependence on insulin signaling as a nerve growth factor during a nerve synapse formation phase about 14 days after the onset of the disturbance. There is the possibility that insulin signals act as key signals in the process of immature olfactory cells being matured; that a lack of this signal could result in incomplete regeneration of olfactory function, thereby leading to a decreased olfactory function.

[II. Odor Substance-Induced c-Fos Expression in OB with Model Mice with Olfactory Disturbance]

On Day 0, methimazole was intraperitoneally injected into mice of each group. 28 days after the administration of methimazole, each mouse was housed in an isolation box, to which clean air was supplied after being deodorized through a charcoal filter. Before an odor substance was given to mice (n=3 mice), the mice were kept in a new cage without being fed with food pellets for four hours.

As three odor substances, aldehyde (propyl aldehyde, n-valeraldehyde, N-heptyl aldehyde, benzaldehyde, and perillaldehyde), lactone (γ-butyrolactone and γ-heptalactone, σ-hexalactone, σ-nonalactone and Y octalactone) and ester (allyl hexanoate, b-γ-hexenyl acetate, terpinyl acetate, and isoamyl acetate) were used. These substances were diluted to a one-tenth of the concentration with mineral oil. Then, cotton paper was immersed in 100 μl of the resulting diluted solution, and was placed in a dish.

Figure 6B:
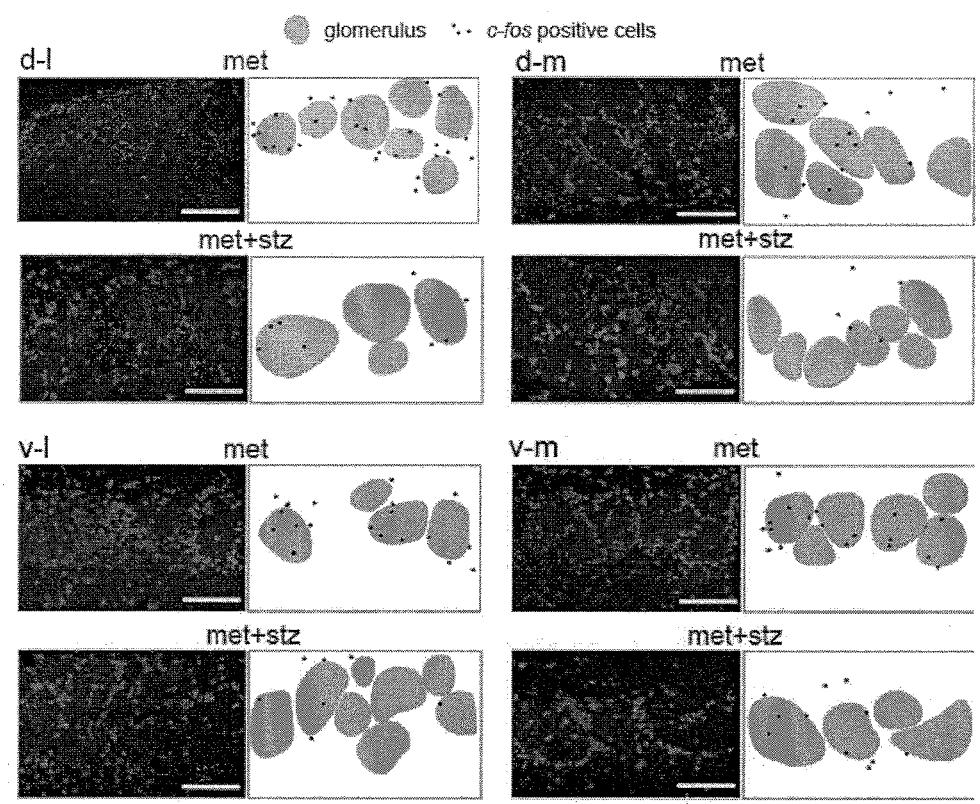
FIG. 6B shows the results of analysis of c-fos expression in OB according to an example.
Figure 6C:
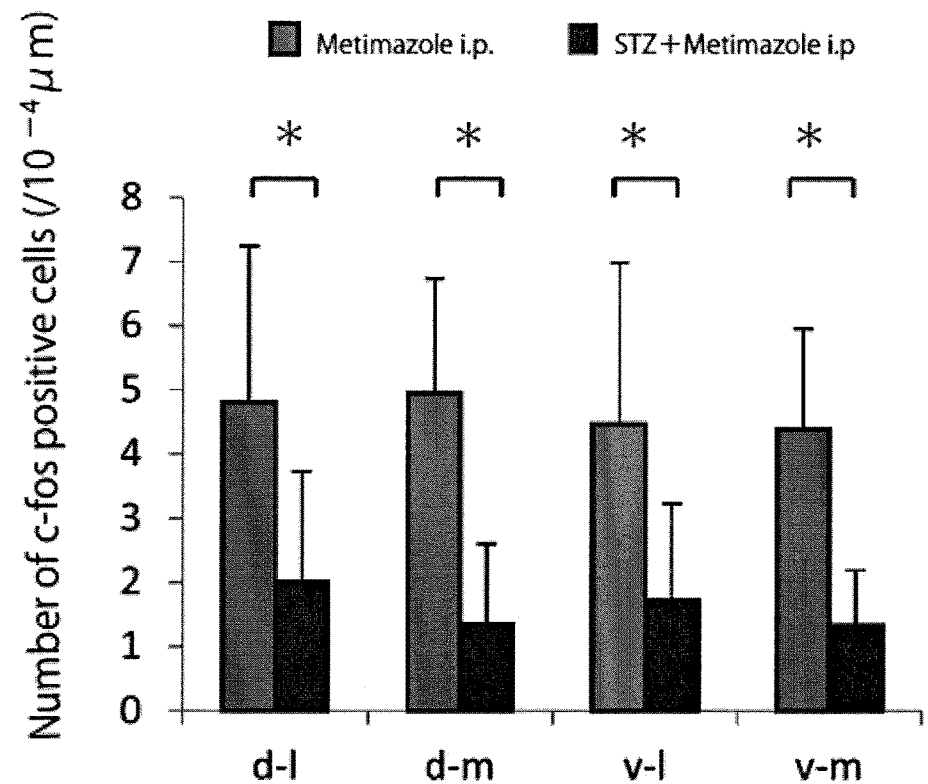
FIG. 6C shows the results of analysis of c-fos expression in OB according to an example.

The odor substances were applied in such a way that the dish was placed in a cage twice per hour at intervals of 10 minutes. After the final odor substances were applied, the mice were perfused with fixative, and were subjected to analysis of c-fos expression in OB. FIGS. 6B and 6C show the results of the analysis of c-fos expression in OB.

As shown in FIGS. 6B and 6C, one month after the onset of an olfactory epithelium disturbance, normal mice were compared with STZ mice in terms of the number of c-fos-positive cells (which are initial-phase response genes in olfactory input and reflect the olfactory function). In the STZ mouse group, a significant decrease in the number of c-fospositive cells was observed. This means that the STZ mice underwent a decrease in the olfactory function in tandem with a delay in the regeneration of olfactory epithelium tissues.

Figure 7A:
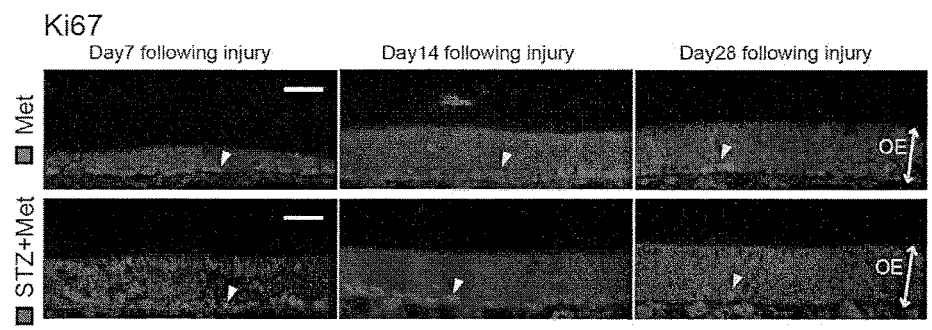
FIG. 7A shows the results of a comparison in the numbers of Ki-67 positive cells during olfactory epithelium regeneration process according to an example.
Figure 7B:
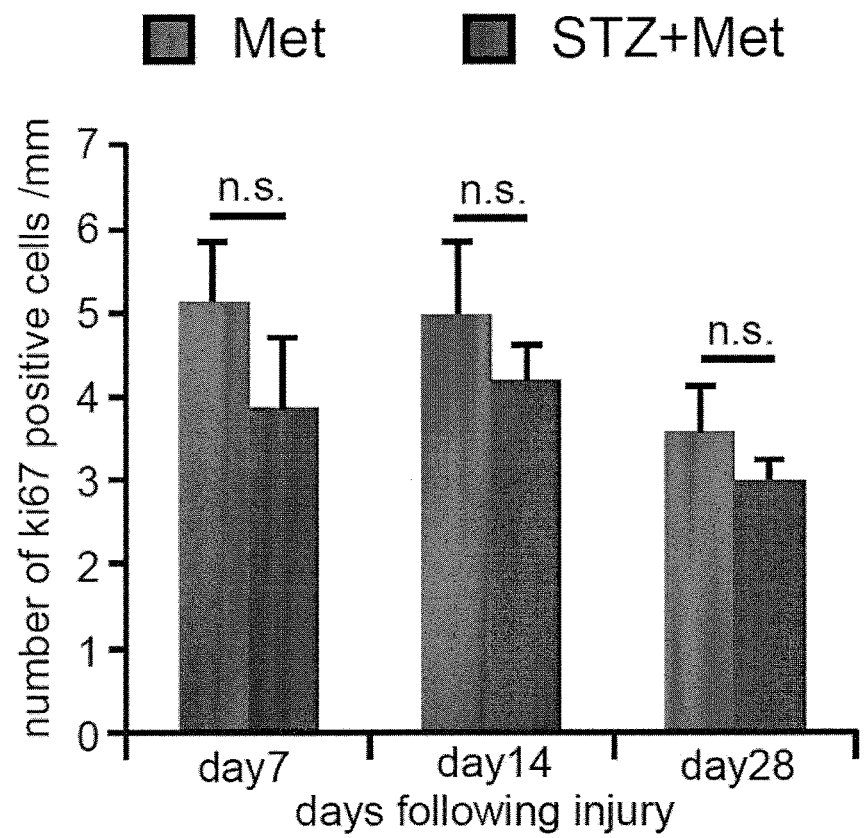
FIG. 7B shows the results of a comparison in the number of Ki-67 positive cells during olfactory epithelium regeneration process according to an example.

FIGS. 7A and 7B show the results of a comparison between the two groups of the number of Ki-67 positive cells in the olfactory epithelium regeneration process. As shown in FIGS. 7A and 7B, between the two groups, a significant difference in the number of Ki-67 positive cells was not observed. This suggests that there was no difference between the two groups in terms of the division capacity of olfactory cells.

Figure 8A:
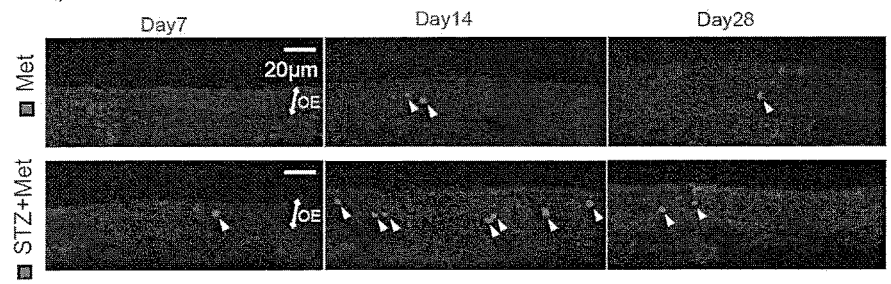
FIG. 8A shows the results of a comparison in the number of activated caspase-3 positive cells during olfactory epithelium regeneration process according to an example.
Figure 8B:
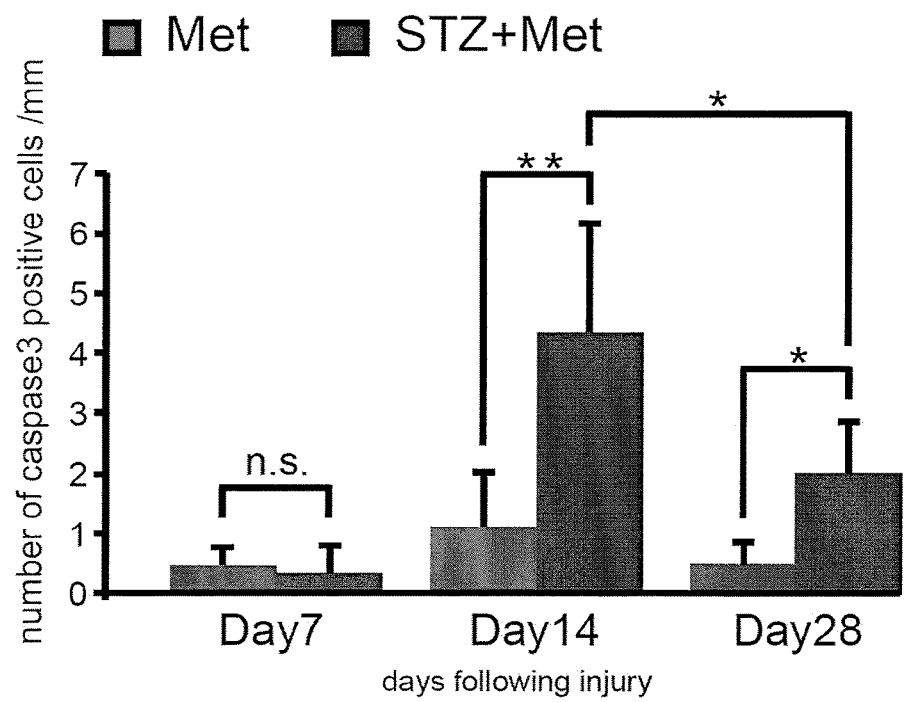
FIG. 8B shows the results of a comparison in the number of activated caspase-3 positive cells during olfactory epithelium regeneration process according to an example.
Figure 8C:
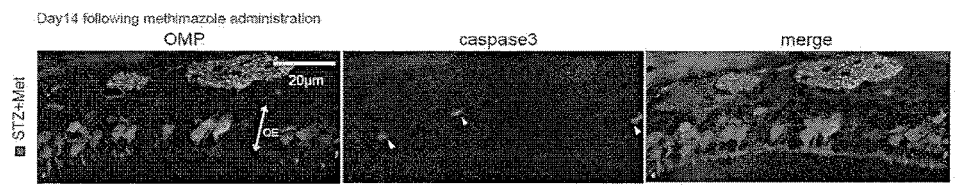
FIG. 8C shows the results of a comparison in the numbers of OMP, activated caspase-3, mergo positive cells 14 days after the administration of methimazole according to an example.

FIGS. 8A and 8B show the results of a comparison between the two groups of the number of activated caspase-3 positive cells (which become positive immediately before going through apoptosis) in the olfactory epithelium regeneration process. It was found that the STZ mouse group showed the number of activated caspase-3 positive cells that becomes peak two weeks after the onset of olfactory epithelium disturbance (There was a significant difference). FIG. 8C shows the results of a comparison in the numbers of OMP, activated caspase-3, and mergo positive cells 14 days after the administration of methimazole. As a result, it was found that, in the second week since the onset of olfactory epithelium disturbance that corresponded to the synapse formation period, immature olfactory cells in the STZ group that lacked insulin signals were unable to form synapses, and that many underwent apoptosis.

[III. Effect of Ameliorating Olfactory Disturbance by Insulin Administration for Model Mice with Type 1 Diabetes (2)]

DM mice were given an insulin preparation, and the effects of improvements on the regeneration and maturing failure of olfactory epithelium were evaluated.

Figure 9A:
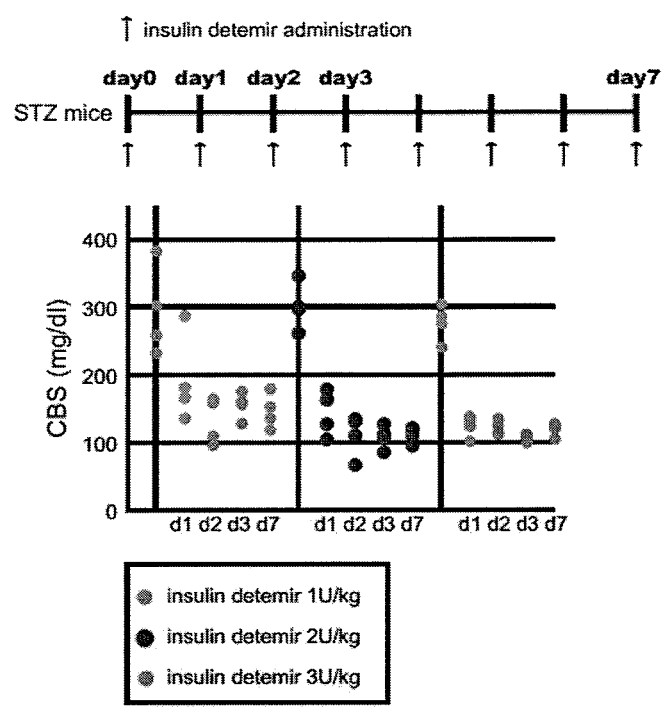
FIG. 9A is a schematic diagram showing the time when a model mouse with olfactory disturbance is replenished with insulin, according to an example.
Figure 9B:
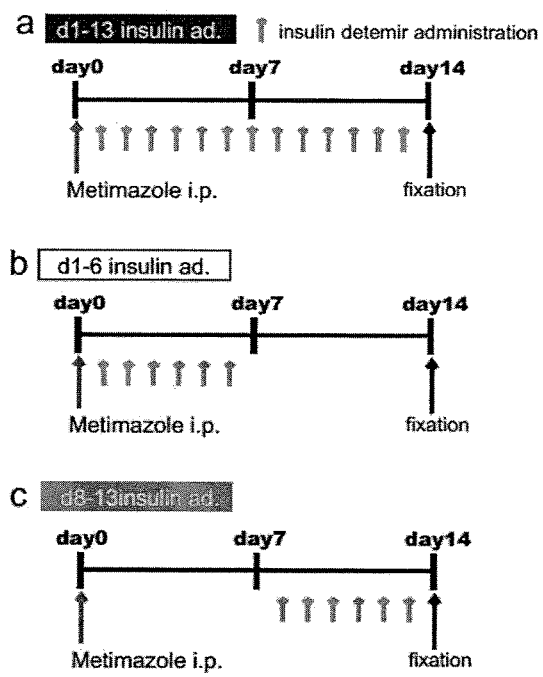
FIG. 9B is a schematic diagram showing the time when a model mouse with olfactory disturbance is replenished with insulin, according to an example.
Figure 9C:
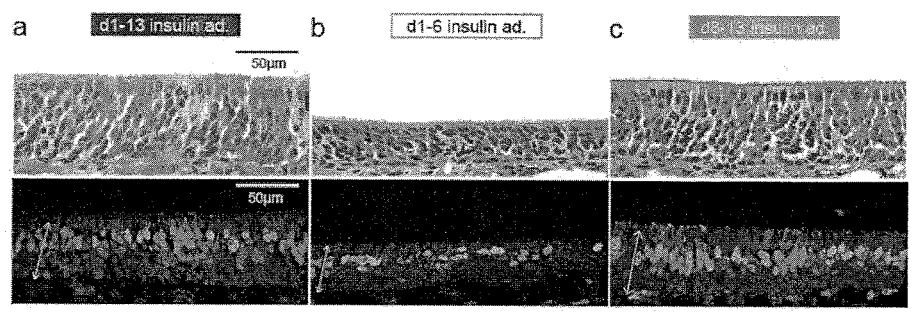
FIG. 9C shows the results of immunostaining on olfactory epithelium after a model DM mouse with olfactory disturbance is given insulin, according to an example.
Figure 9D:
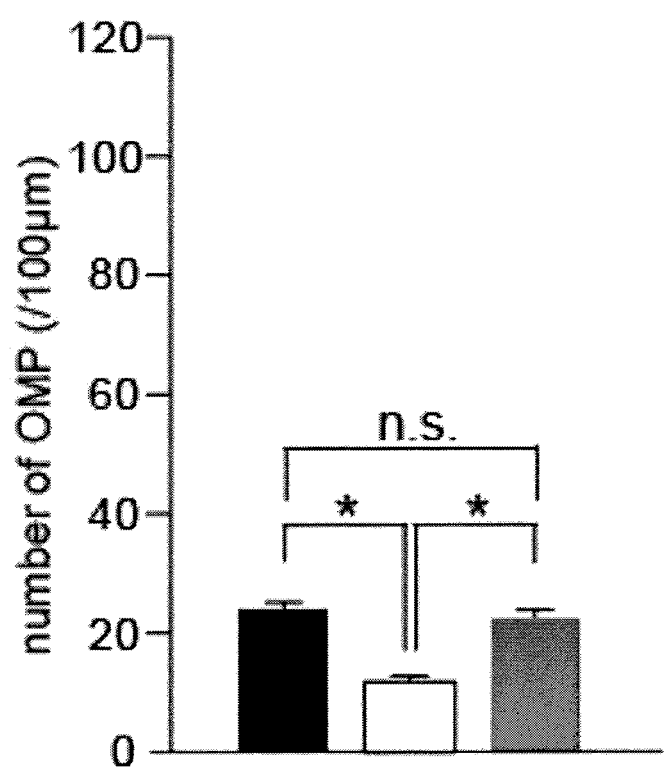
FIG. 9D shows the results of analysis on the number of OMP-positive cells of olfactory epithelium after a model DM mouse with olfactory disturbance is given insulin, according to an example.
Figure 9E:
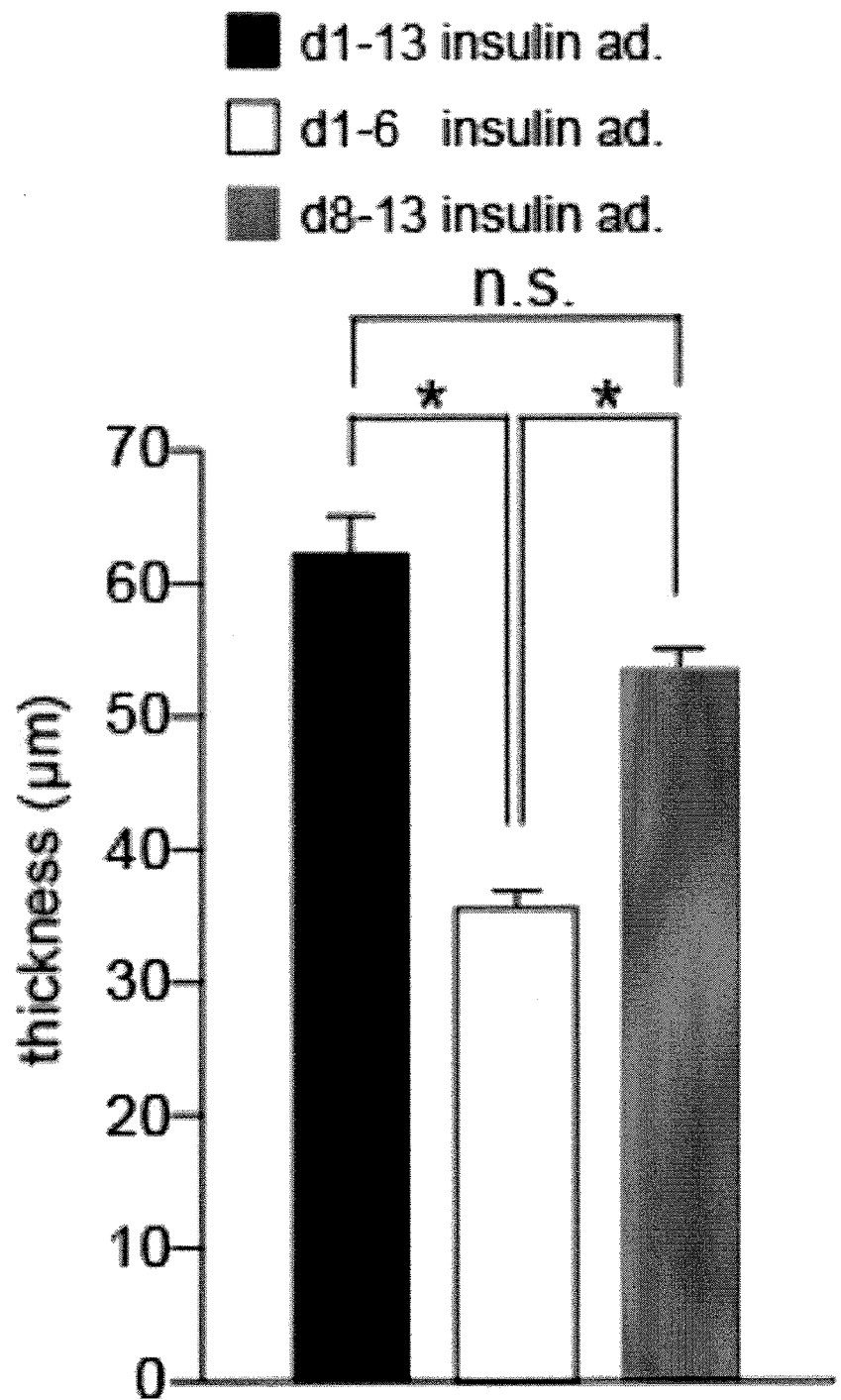
FIG. 9E shows the results of analysis on the thickness of olfactory epithelium after a model DM mouse with olfactory disturbance is given insulin, according to an example.
Figure 9F:
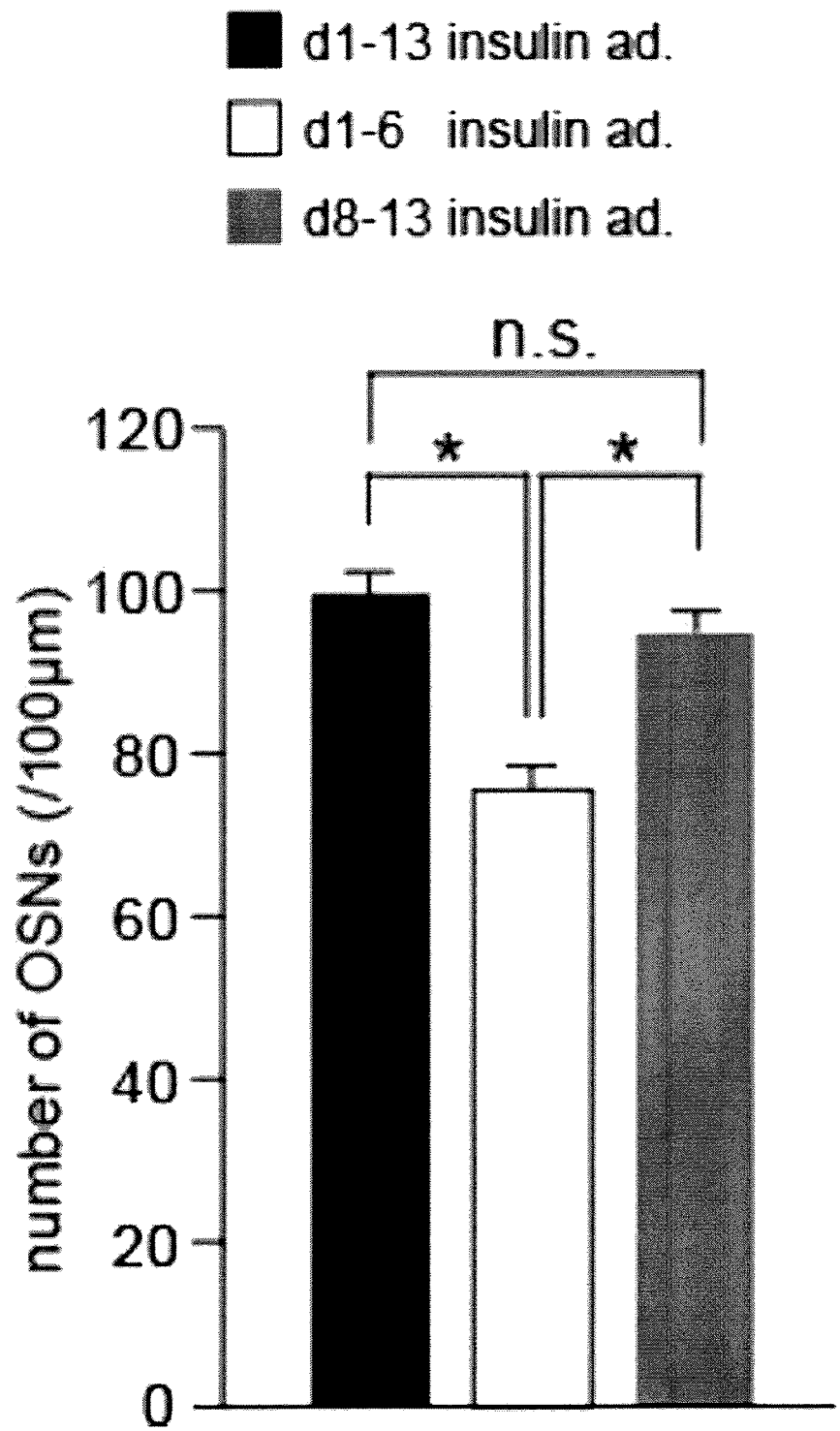
FIG. 9F shows the results of analysis on the number of olfactory nerve cells (OSNs) of olfactory epithelium after a model DM mouse with olfactory disturbance is given insulin, according to an example.

As the insulin preparation, "Levemir FlexPen (Registered Trademark)" was used (referred to as Levemir). Levemir was administered intraperitoneally into DM mice once a day, with 2 to 3 U/kg of the insulin detemir each. As a result, the DM mice showed improvements in terms of high blood sugar, and their blood sugar levels were kept at about the normal level, or around 130 mg/dl. The amount of insulin given here was therefore regarded as the amount that can properly resolve the shortages of insulin in the DM mice. The olfactory epithelium tissues of groups of DM mice (group a, group b, and group c) were observed 14 days after the administration of methimazole (Refer to FIGS. 9A and 9B): Each group differs on the time when insulin was additionally given. As shown in FIGS. 9A and 9B, group a is the group in which 3 U/kg of insulin detemir was administered intraperitoneally and added every day from the first day to 14$^{th}$ day since the administration of methimazole; group b is the group in which 3 U/kg of insulin detemir was administered intraperitoneally only from the first day to 7th day since the administration of methimazole; and group c is the group in which it was administered intraperitoneally only from the 7th day to 14th day. 14 days after the administration of methimazole, all mice of groups a to b were fixed with paraffin. Then, with the use of the above-described method, the number of olfactory nerve cells (OSNs) of olfactory epithelium, the thickness of olfactory epithelium, and the number of OMP positive cells were counted in each group. FIGS. 9C to 9F show the results.

As a result, in groups a and b, 14 days after the administration of methimazole, DM mice were broadly comparable to normal mice in terms of the number of mature olfactory nerve cells (the number of OMP positive cells). Moreover, in terms of the thickness of olfactory epithelium and the number of olfactory nerve cells, there was no significant difference between the normal mice and the DM mice.

As shown in FIGS. 9C to 9F, 14 days after the onset of the disturbance, only in group b, there were significant decreases compared with groups a and c, in terms of the thickness of olfactory epithelium and the numbers of OSNs and OMP positive cells. In groups a and c, no significant differences were observed in terms of the thickness of olfactory epithelium and the numbers of OSNs and OMP positive cells. This suggests that insulin signals are not important between Day 0 and Day 7 after the onset of olfactory epithelium disturbance, and that the existence of appropriate insulin signals in the days 7 to 14 after the onset of olfactory epithelium disturbance (which corresponds to the synapse formation period) may be a factor in ensuring the normal differentiation and maturing of the olfactory epithelium in subsequent processes. This suggests that the dependence on insulin signals is likely to increase especially during the synapse formation period.

Figure 10A:
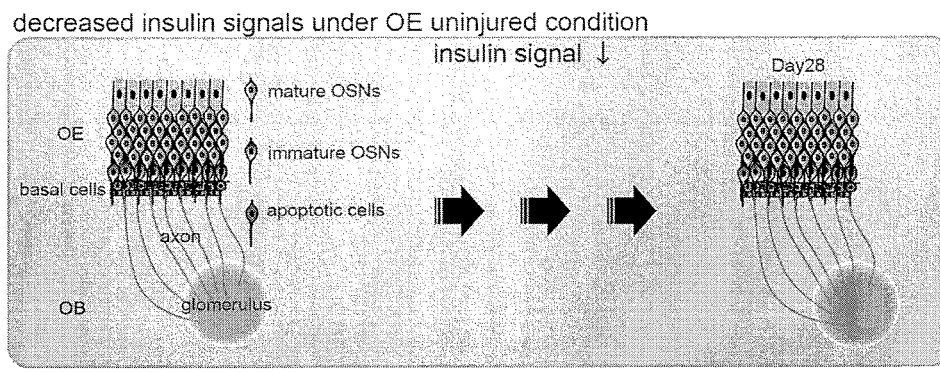
FIG. 10A is a diagram schematically showing a decrease of insulin signaling under an OE non-disabled state, based on the overall results of the examples.
Figure 10B:
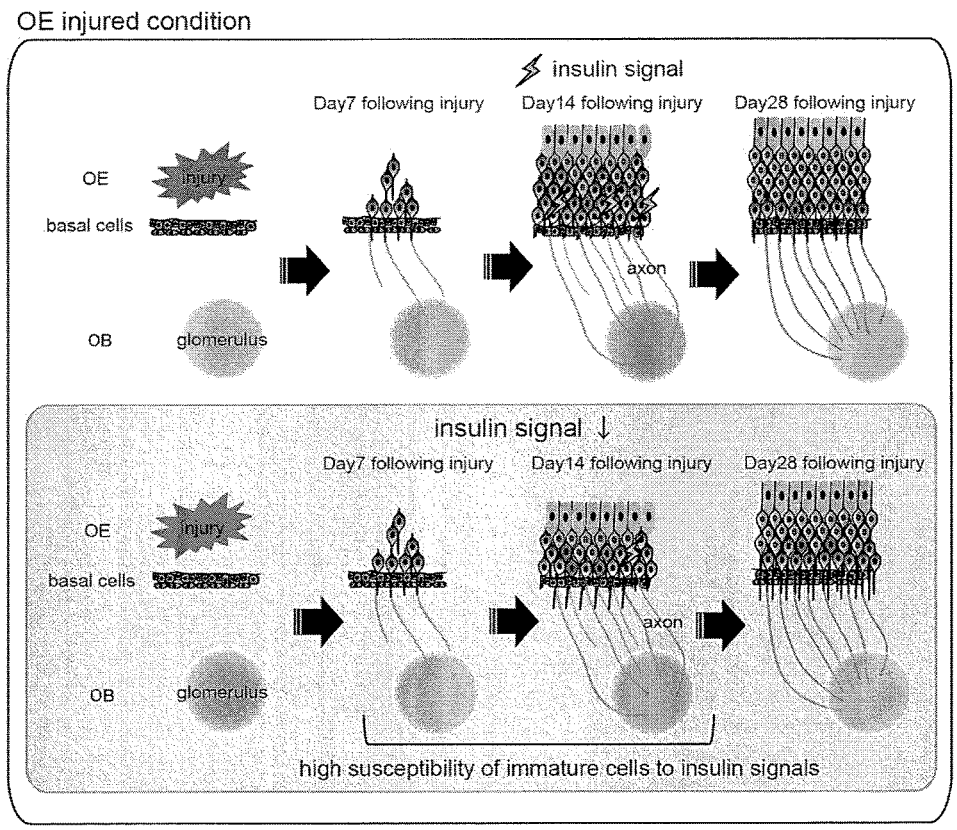
FIG. 10B is a diagram schematically showing an OE-disabled state based on the overall results of the examples.

Based on the above-mentioned results, it was found that whether there are insulin signals in the synapse formation period will determine the future of the olfactory epithelium regeneration (Refer to FIG. 10A). Moreover, the results suggest that the dependence on insulin signals could increase during the synapse formation period (Refer to FIG. 10B). Nerve stimulation factors have heretofore been considered to be constantly functioning to a certain degree. However, the inventors have for the first time found that the dependence varies according to the time.

The olfactory disturbance therapeutic agent of the present invention contributes to the health and welfare of people with olfactory disturbance, as well as to the overall national economy, such as reducing costs of medicine associated with olfactory disturbance and preventing a decrease in the labor force.

What is claimed is:

1. A method of treating an olfactory disturbance using a therapeutic agent comprising:
   administrating the agent to a patient in need thereof, comprising at least one active ingredient that is selected from the group consisting of insulin, insulin alpart, insulin lispro, insulin glulisine, insulin degludec, insulin glargine, insulin detemir, and their pharmaceutically acceptable salts, wherein the agent is administrated at least in the days 7 to 14 after the onset of olfactory epithelium disturbance.

2. The method of treating an olfactory disturbance according to claim 1, wherein the agent is used for people with olfactory disturbance who have impaired insulin secretion or insulin resistance.

* * * * *